US008855947B2

(12) United States Patent
Sheila-Vadde et al.

(10) Patent No.: US 8,855,947 B2
(45) Date of Patent: Oct. 7, 2014

(54) MULTIPHASE FLOW METERING WITH PATCH ANTENNA

(75) Inventors: Aparna Chakrapani Sheila-Vadde, Bangalore (IN); Prafull Sharma, Bangalore (IN); Manoj Kumar Koyithitta Meethal, Bangalore (IN); Mandar Diwakar Godbole, Bangalore (IN)

(73) Assignee: General Electric Company, Niskayuna, NY (US)

( * ) Notice: Subject to any disclaimer, the term of this patent is extended or adjusted under 35 U.S.C. 154(b) by 816 days.

(21) Appl. No.: 12/916,149

(22) Filed: Oct. 29, 2010

(65) Prior Publication Data

US 2011/0196625 A1  Aug. 11, 2011

Related U.S. Application Data

(60) Provisional application No. 61/302,381, filed on Feb. 8, 2010.

(51) Int. Cl.
*G01F 1/66* (2006.01)

(52) U.S. Cl.
USPC .......................................................... 702/49

(58) Field of Classification Search
USPC ............. 702/23, 45, 49, 50, 72, 75, 100, 159, 702/172; 73/861.08; 324/640, 663
See application file for complete search history.

(56) References Cited

U.S. PATENT DOCUMENTS

| 4,062,010 | A | * | 12/1977 | Young et al. ..................... 342/21 |
| 4,902,961 | A | | 2/1990 | De et al. |
| 5,485,743 | A | | 1/1996 | Taherian et al. |
| 5,675,259 | A | | 10/1997 | Arndt et al. |
| 7,135,872 | B2 | * | 11/2006 | Bentolila et al. .............. 324/640 |
| 7,293,471 | B2 | | 11/2007 | Lund Bo et al. |
| 7,712,381 | B2 | | 5/2010 | Allenberg et al. |
| 2008/0087099 | A1 | * | 4/2008 | Allenberg et al. ......... 73/861.08 |
| 2008/0319685 | A1 | | 12/2008 | Xie et al. |
| 2009/0126502 | A1 | * | 5/2009 | Wee et al. .................. 73/861.04 |
| 2010/0148804 | A1 | * | 6/2010 | Jakoby et al. ................. 324/663 |

FOREIGN PATENT DOCUMENTS

| CN | 101103256 A | 1/2005 |
| CN | 101548179 A | 9/2009 |
| WO | 0077501 A1 | 12/2000 |
| WO | 2008069670 A1 | 6/2008 |

OTHER PUBLICATIONS

S. R. Wylie et al., "RF sensor for multiphase flow measurement through an oil pipeline," Institute of Physics Publishing, Measurement Science and Technology, vol. 17, 2006, pp. 2141-2149.

Unofficial English translation of Office Action issued in connection with corresponding CN Application No. 201110078762.X on Jan. 22, 2014.

* cited by examiner

*Primary Examiner* — Mohamed Charioui
(74) *Attorney, Agent, or Firm* — Seema S. Katragadda

(57) ABSTRACT

Various methods of metering a multi-phase composition in a pipe using patch antenna(s), that operate in a radio or microwave frequency range, are disclosed including locating and then exciting the patch antenna(s) over a range of frequencies; measuring transmitted and reflected signals over time; estimating a shift in a resonant frequency from a baseline resonant frequency; then calculating a permittivity of the composition, based on the shift; and calculating a phase composition of the multi-phase composition. The present invention has been described in terms of specific embodiment(s), and it is recognized that equivalents, alternatives, and modifications, aside from those expressly stated, are possible and within the scope of the appending claims.

13 Claims, 10 Drawing Sheets

MULTIPHASE FLOW METERING WITH PATCH ANTENNA

CROSS-REFERENCE TO RELATED APPLICATIONS

This application claims priority to, U.S. patent application Ser. No. 61/302,381, filed Feb. 8, 2010, assigned, the contents of which are hereby incorporated by reference in their entirety.

BACKGROUND OF THE INVENTION

The present invention relates generally to multiphase flow metering, and more specifically, to the use of patch antennas in the metering of multiphase compositions.

In process industries, oil and gas industries and other such areas, it is often necessary to accurately measure the composition and flow rate of material flowing inside a pipeline. In cases where the electrical conductivity of the medium is very low, for instance wet-gas flows, where the composition has a small percentage of oil and/or water, and the change in dielectric constant with fractional changes in oil/water is very small, it becomes difficult to measure changes in composition.

Commercially available sensors for measuring fluids in the petroleum industry are based on a variety of principles (either a single technique or a combination of several techniques). For example, impedance sensors, capacitive and/or inductive sensors, dual-energy gamma sensors, venturi meters, and microwave sensors (attenuation/phase/resonance) have all been used. Currently, there are numerous microwave-based flow metering sensors available offering varying degrees of sensitivity, complexity and costs. Typically, measurement of amplitude and phase of the signals is used to reconstruct various flow regimes, such as slug, churn, and annular. With all the methodologies of measuring multiphase flow, accuracy, sensitivity, cost and technical complexity is a concern.

Accordingly, there is an ongoing need for improving upon multiphase flow metering.

BRIEF DESCRIPTION

The present invention overcomes at least some of the aforementioned drawbacks by providing an improved method and system for flow metering of a multiphase composition. More specifically, aspects of the present invention may use one, or more, patch antenna(s) to obtain information from a multiphase composition flowing in a pipe.

Therefore, according to one embodiment of the present invention, a method of metering a multi-phase composition in a pipe, comprises locating at least one patch antenna that operates in a radio or microwave frequency range; in proximity to the multi-phase composition; exciting the at least one patch antenna over a range of frequencies; measuring transmitted and reflected signals over time; estimating a baseline resonant frequency; estimating a shift in a resonant frequency from the baseline resonant frequency; calculating a permittivity of the multi-phase composition, based on the shift; and calculating a phase composition of the multi-phase composition, based on the permittivity.

According to another embodiment of the present invention, a method of metering a multi-phase composition flowing through a pipe, the method comprises: locating at least one patch antenna in communication with the multi-phase composition, wherein the at least one patch antenna operates in a radio or microwave frequency range; exciting the at least one patch antenna over a range of frequencies; measuring transmitted and reflected power over the range of frequencies; estimating a phase fraction of the multi-phase composition, based on amplitude and phase measurements.

According to another embodiment of the present invention, a method of metering a multi-phase composition flowing through a pipe comprises locating a plurality of patch antennas that operate in a radio or microwave frequency range in proximity to the multi-phase composition; exciting the plurality of patch antennas over at least one frequency, thereby creating a transmitted and a reflected signal; estimating a flow regime based on a signature of the transmitted and reflected signals; and calculating a phase composition of the multi-phase composition, based on the transmitted and reflected signals.

According to another embodiment of the present invention, a method of metering a multi-phase composition flowing through a pipe, the method comprises locating a plurality of patch antenna sets axially along a pipe, wherein a first patch antenna set is placed axially a distance from the second patch antenna set; exciting the plurality of patch antennas sets over a range of frequencies; measuring power at the plurality of patch antennas sets over at least one of the range of frequencies; and estimating a velocity of the flowing multi-phase composition, based on the measuring.

According to another embodiment of the present invention, a method of metering a multi-phase composition flowing through a pipe comprises obtaining a plurality of measurands from the multi-phase composition, wherein the plurality of measurands comprise at least one of amplitude, phase, and frequency measurements; combining the plurality of measurands into a single quantity by using a transfer function; and estimating a phase fraction of the multi-phase composition, based on the single quantity.

According to another embodiment of the present invention, a method of metering a multi-phase composition flowing through a pipe comprises locating a plurality of patch antennas that operate in a radio or microwave frequency range in proximity to the multi-phase composition; and using the plurality of patch antennas to serve as electrodes, thereby obtaining low frequency impedance measurements of the multi-phase composition.

Various other features and advantages of the present invention will be made apparent from the following detailed description and the drawings.

BRIEF DESCRIPTION OF THE DRAWINGS

The drawings illustrate one embodiment presently contemplated for carrying out the invention.

DETAILED DESCRIPTION

Figure 1:
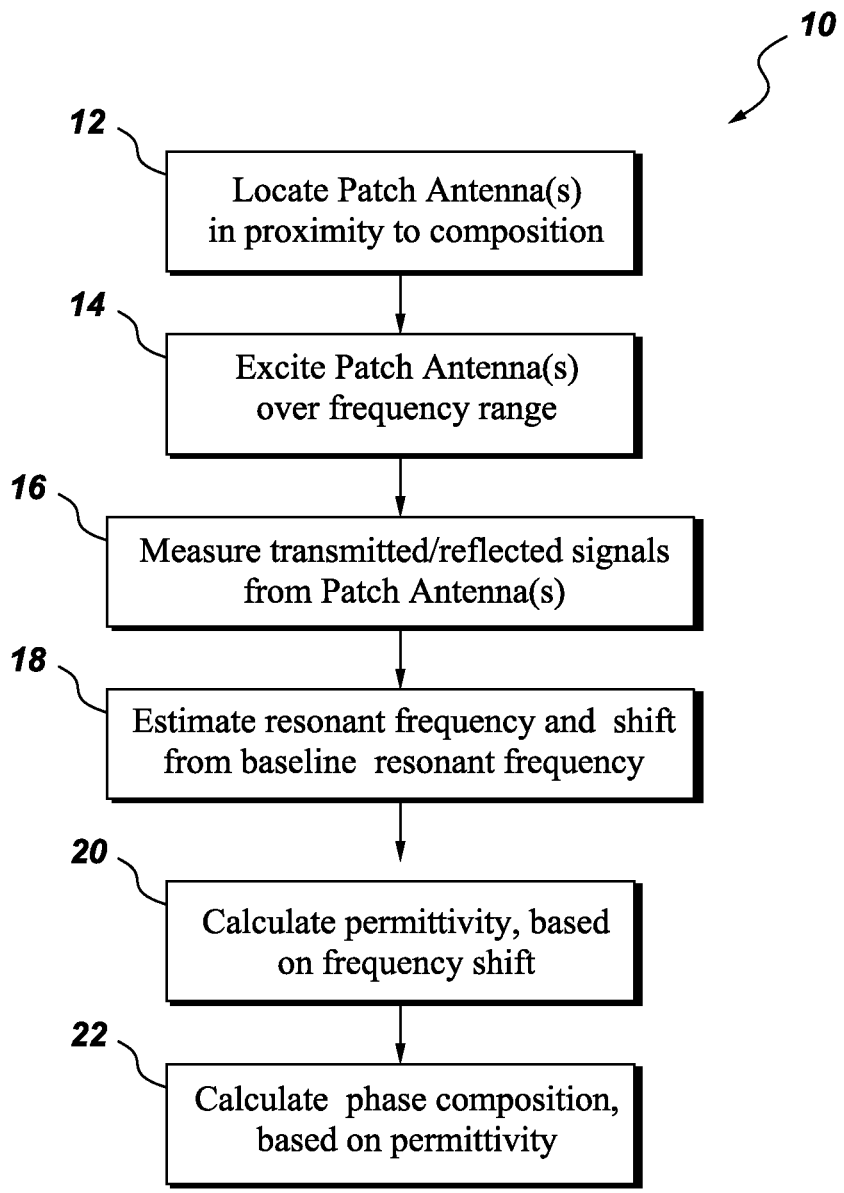
FIG. 1 is a flowchart of a method of multiphase flow metering, according to an embodiment of the present invention.

Aspects of the present invention provide a technique for measurement of frequency changes that is more robust as compared to amplitude/phase measurements. The invention offers a non-intrusive, non-contact method that can probe non-conducting materials consisting predominantly of, for example, oil or gas.

Aspects of the present invention relate to a method for measuring the composition of multiphase mixtures by using one or more patch antennas operating in the RF/microwave frequency range. In one of the potential applications, the multiphase mixture could be flowing in a pipeline. In the case of a metallic pipe, the antennas will be on the inner surface and in the case of a non-metallic pipe/spool, the antennas can be on the outer surface say, as a strap-on. One novel aspect is the use of patch antennas resulting in a non-intrusive, low pressure loss measurement. Additionally, the patch antennas can serve as electrodes for low frequency impedance measurements. Transmission, reflection or resonant methods may be used with amplitude, frequency or phase as measurands. Resonant frequency measurements are found to be more robust as compared to amplitude and phase measurements, which are more prone to noise. Aspects of the present invention focus on the resonant frequency approach. However, in another embodiment a configuration of patches may be used for amplitude/phase measurements without depending on resonance and an array of patches can provide a tomographic reconstruction of the multiphase mixture flowing inside the pipe.

For purposes of this application and invention, there are various definitions that are germane. The term "patch antenna", as used herein, means a transmitting and/or receiving element that is capable at operating at high frequencies (e.g., about 1 GHz to about 20 GHz) comprising two parallel conductors, a metal patch over a ground plane, separated by a dielectric layer or substrate therebetween. The substrate can be flexible in which case it can conform to the pipe inner surface. In microstrip patches, the metal patch is printed onto the dielectric. Microstrip patches have the advantage of being lightweight, inexpensive and easy to integrate with other electronics. The term "multi-phase" and "multiphase", as used herein, means a composition that comprises at least two phases of material. The multiphase composition may comprise some combination of oil, water, and gas. For example, the composition may comprise gas and water. The composition may comprise gas and oil. The terms "radio or microwave frequency range", as used herein, means electromagnetic frequency between hundreds of MHz to several tens of GHz. The term "pipe", as used herein, means any structure wherein a flow of a multiphase composition is possible. That is the term is not limited to elements that are substantially round in cross-section, substantially closed, longitudinal elements (e.g., the term as used in sanitary or plumbing engineering).

In some oil and gas applications, the pipe contains a mixture of two materials, for example, gas and liquid (e.g., oil/water) or an emulsion of oil and water. In an embodiment, one or more patches are excited over a range of frequencies and the reflected and/or the transmitted power is measured over that frequency range. For a given pipe diameter, the resonant frequency of the system depends on the permittivity (dielectric constant) of the medium inside the pipe. The dielectric property is a complex quantity, which is frequency dependent. The real part, of the dielectric constant, is an indication of how easily the material can be polarized in the presence of an electric field. The imaginary part, of the dielectric constant, represents the losses in the medium. A resonant mode can be characterized by the resonant frequency, Q factor and the amplitude of the peak. The shift in resonant frequency with a change in composition is used to estimate the phase fraction of the mixture. In addition, the quality factor (Q) of resonance and the amplitude of the resonance peak can also be used. The resonant frequency is inversely proportional to the real part of the dielectric constant. The amplitude and sharpness of the resonance peak, quantified by the Q factor are inversely proportional to the imaginary part of the dielectric constant. For instance, as the water content increases, the effective dielectric constant increases and the resonant frequency decreases. Similarly, if the water is lossy, e.g., due to salinity, that will result in a decrease in the peak amplitude and increase in the width of the peak. Estimation of phase fractions using the resonant frequency method becomes difficult as the water content increases since identification of the peaks (resolution) becomes a challenge.

To estimate the flow velocity, resonant frequency at two locations along the axis of the pipe can be measured with two sets of patches and cross-correlation techniques can be used. A similar approach can be used in the case of tomographic reconstruction.

Aspects of the present invention use one or more patches antennas, operating in the RF/microwave frequency range, to measure the phase fraction/flow rate of the constituents flowing inside a pipe. The patches can be excited over a range of frequencies and resonant modes will be set up at some frequencies depending on the dimensions of the pipe, the patch configuration and the dielectric properties of the material inside the pipe.

In an embodiment, each of the patches will conform to the inner wall of the pipe making the design non-intrusive. A patch operating as an antenna in high frequencies may comprise two parallel conductors, a metal patch over a ground plane, separated by a dielectric layer in between. In the case of the patches for flow metering, the ground plane can be the same as the stainless steel pipe. One way to feed the patch would be to use a co-axial cable connected from the back of the patch.

Aspects of the method were tested using simulations and experiments. In one experiment, the mixture inside the pipe consists of gas and oil and small changes in oil fraction (<10%) needed to be determined accurately. In this case, the permittivity contrast is much smaller as opposed to the case of oil/water or gas/water since the dielectric constant of water (approximately 80) is much higher than that of oil (approximately 2.2) and natural gas (approximately 1). Simulations as well as experiments show that even small permittivity changes translate to measurable frequency shifts. Experiments were also done on a mixture of two oils whose dielectric constants are close to each other. Small changes in dielectric constant corresponding to small changes in phase fraction (0 to 5%), resulted in consistent and finite frequency shifts which were measurable.

In another configuration, the patch antennas can be placed inside a cavity that surrounds a section of the pipe. In this case, the resonant frequency can be partly controlled by the size of the cavity and the quality factor could be better than in the case of an open pipe. However, impedance matching becomes trickier and the coupling efficiencies would be lower as compared to the case when the patches are inside the pipe.

In still another configuration, if the pipe is non-metallic or if there is a non-metallic spool, the patches can be mounted on the outer surface of the pipe/spool. This embodiment can provide a strap-on type of solution.

Further, the shape is not restricted to a square and can potentially be any other shape that meets the requirements. Similarly, the polarization of the antennas can also be different and can potentially be circular, elliptical or other polarizations.

FIG. 1 depicts a flowchart of a method for measuring multiphase flow using patch antennas, in accordance with aspects of the present invention. The method 10 comprises locating a plurality of patch antennas 30 in communication and/or proximity to a multiphase composition flow at 12. The plurality of patch antennas 30 typically are capable of operating in at least radio and/or microwave frequency range.

At 14 a frequency sweep is applied to the plurality of patch antennas 30, wherein the patch antennas 30 are exciting over a range of frequencies.

The plurality of patch antennas 30 creates electromagnetic fields as a result and set up resonance at certain frequencies. At 16 the method 10 comprises measuring the transmitted and reflected signals from plurality of patch antennas 30. Based on the measurement at 16, at 18 the resonant frequency is estimated or calculated, as is the shift from the baseline resonant frequency.

Then at 20, the permittivity of the multiphase composition is calculated based on the estimated/calculated frequency shift. The permittivity may be found by applying a transfer function.

At 22, the phase percentage composition of the multiphase composition is calculated, based on the permittivity found at 20. The phase composition may be calculated by applying transfer functions, such as Brueggman, Maxwell Garnet, and the like.

FIGS. 2A through 2D depict perspective views of various exemplary patch antenna systems that may be used to measure multiphase flow in accordance with aspects of the present invention. For example, the embodiment in FIG. 2A, termed an "inline patch", comprises a pipe 100 and a plurality of patch antennas 30 configured in a substantially linear configuration. The plurality of patch antennas 30 may be configured to substantially surround the circumference of the pipe 100. The inline patch of patch antennas 30 may be located, for example, on an inside surface of a substantially metal pipe 100. The inline patch may be installed within a new pipe 100 prior to use or installed in an existing pipe 100 using a spool piece for instance (e.g., during temporary shutdown), thereby offering a retrofit solution.

Figure 2A:
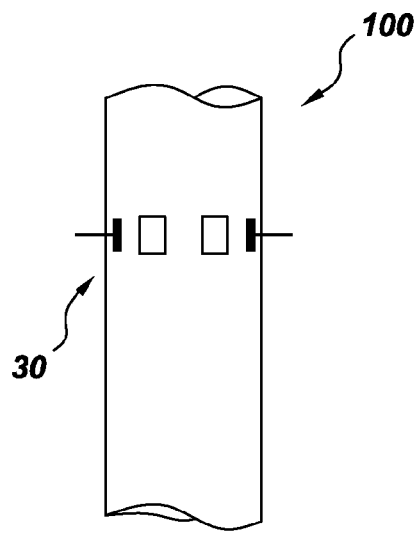
FIGS. 2A-2D are perspective views of portions of pipelines using patch antennas, according to various embodiments of the present invention.
Figure 2B:
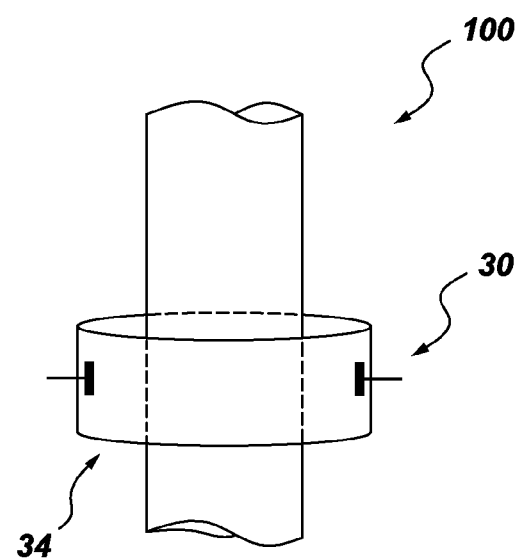

The embodiment in FIG. 2B, termed a "cavity patch", comprises a pipe 100 and a plurality of patch antennas 30 configured such that a cavity exists between the plurality of patch antennas 30 an outer surface of the pipe 100. The plurality of patch antennas 30 comprise at least a transmitter antenna 30 and a receiver antenna 30. A cavity patch 34 that includes the plurality of patch antennas 30 attached thereto may be installed along a portion of the pipe 100. Portions of the cavity patch 34 may or may not contact the pipe 100, which is non-metallic. The cavity patch 34 may be installed around a new pipe 100 prior to use or installed around an existing pipe 100 (e.g., during temporary shutdown), thereby offering a retrofit solution.

Figure 2C:
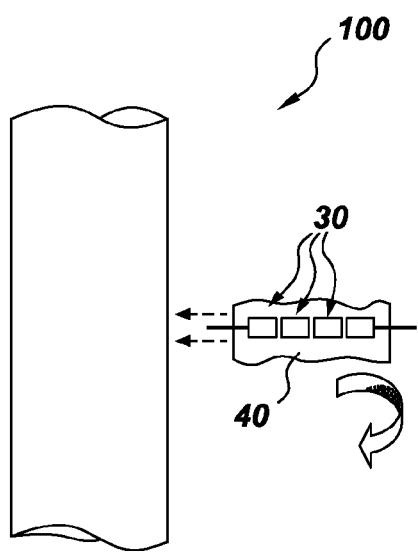

The embodiment in FIG. 2C, termed a "patch strap", comprises a pipe 100 and an element 40 (e.g., "patch strap") comprising a plurality of patch antennas 30 configured such that the element may be installed around an outer surface of the pipe 100 (e.g., wrapped around the pipe 100). The element 40 may be made of any suitable material to allow the element 40 to adequately flex and/or wrap around the circumference of the pipe 100. Typically, the patch strap embodiment may be employed in situations wherein the pipe 100 is non-metallic (e.g., plastic, glass, ceramic, etc.) or has sections that are non-metallic. The element 40 that includes the plurality of patch antennas 30 attached thereto may be installed along a portion of the pipe 100. The plurality of patch antennas 30 may be configured in a substantially linear arrangement so that the plurality of patch antennas substantially surround the pipe 100 when the element 40 is attached to the pipe 100 (see e.g., FIG. 2C). The element 40 may be installed around a new pipe 100 prior to use or installed around an existing pipe 100 (e.g., during temporary shutdown), thereby offering a retrofit solution.

Figure 2D:
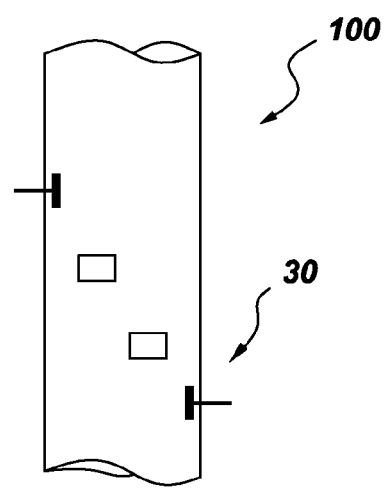

The embodiment in FIG. 2D, termed a helical patch, comprises a pipe 100 and a plurality of patch antennas 30 configured in a substantially helical arrangement. The plurality of patch antennas 30 may be configured to substantially surround the circumference of the pipe 100. The helical patch of patch antennas 30 may be used, for example, on an inside surface of a substantially metal pipe 100 or on an outside surface of a substantially nonmetallic pipe 100. The inline helical patch may be installed within or on a new pipe 100 prior to use or installed in or on an existing pipe 100 (e.g., during temporary shutdown), thereby offering a retrofit solution. Clearly, other embodiments and configurations of patch antennas 30 from those illustrated may be used without departing from aspects of the present invention.

Figure 3A:
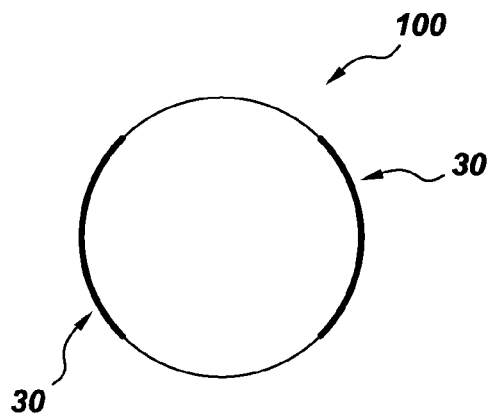
FIGS. 3A-3C are end views of portions of pipelines using patch antennas, according to various embodiments of the present invention.
Figure 3B:
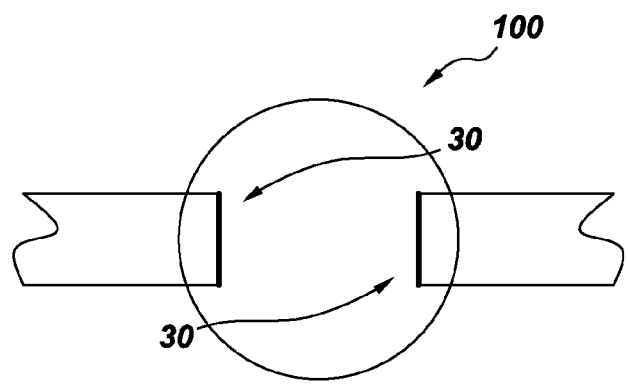
Figure 3C:
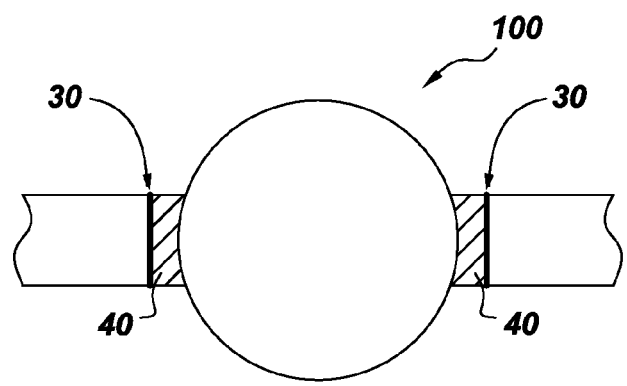
Figure 4A:
FIGS. 4A-4F are views of various patch antenna shapes, according to various embodiments of the present invention.
Figure 4B:
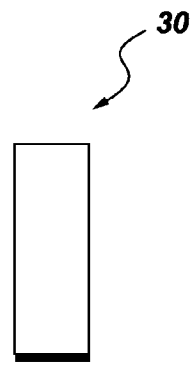
Figure 4C:
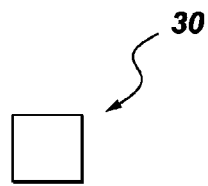
Figure 4D:
Figure 4E:
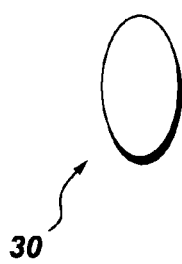
Figure 4F:
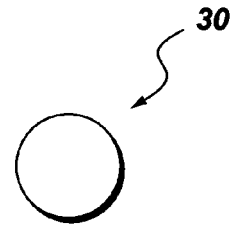

FIGS. 3A through 3C depict end sectional views of a pipeline 100 employing various embodiments of the present invention. Different configurations of employing patch antennas 30 are depicted. For example, FIG. 3A depicts patch antennas 30 that are constructed on a flexible substrate, thereby allowing the patch antenna 30 to conform to the shape (e.g., curved) of the pipe 100. The pipe 100 in certain embodiments may be non-planar. This embodiment allows close or exact conformance between the shape of the patch antenna 30 and the pipe 100 to which it is attached. FIG. 3B depicts patch antennas 30 that may protrude partially into the interior flow space of the pipe 100. A substrate material of the patch antenna 30 in this embodiment may be rigid. FIG. 3C depicts patch antennas 30 that are recessed away from the interior flow space of the pipe 100. A material 40 that is substantially transparent to microwaves may be placed between the patch antennas 30 and the interior flow space of the pipe 100. In another embodiment, the patch antennas 30 may be removably attachable to the pipe 100. In still other embodiments the patch antennas 30 may further include a protective cover and/or radome on it so as to provide additional protection from various factors (e.g., erosion, corrosion, etc.). Clearly, other embodiments may be employed using some combination of the aforementioned features without departing from aspects of the invention.

FIGS. 4A through 4F depict some of the shapes of patch antennas 30 that may be used in accordance with aspects of the present invention. The shape of the patch antenna 30 may be virtually any polygonal shape or combination thereof. For example, the patch antenna 30 may be rectangular (e.g., FIGS. 4A-4C), square (e.g., FIG. 4C), circular (e.g., FIG. 4F), elliptical (e.g., FIGS. 4D-4F), and the like, or combinations thereof. As shown, a primary axis of the patch antenna 30 may be either substantially parallel with the longitudinal axis of the pipe (e.g., FIGS. 4A, 4D) or the primary axis of the patch antenna 30 may be substantially normal to the longitudinal axis of the pipe (e.g., FIGS. 4B, 4E). Similarly, in addition to the physical shape of the patch antennas 30 employed, patch antennas 30 with different polarizations may be used. For example, the polarization of the patch antennas 30 may be elliptical, circular, linear, and the like. It should be obvious that the shape(s) the patch antenna(s) 30 used herein may be different than those shown, without departing from the aspects of the present invention.

Figure 5:
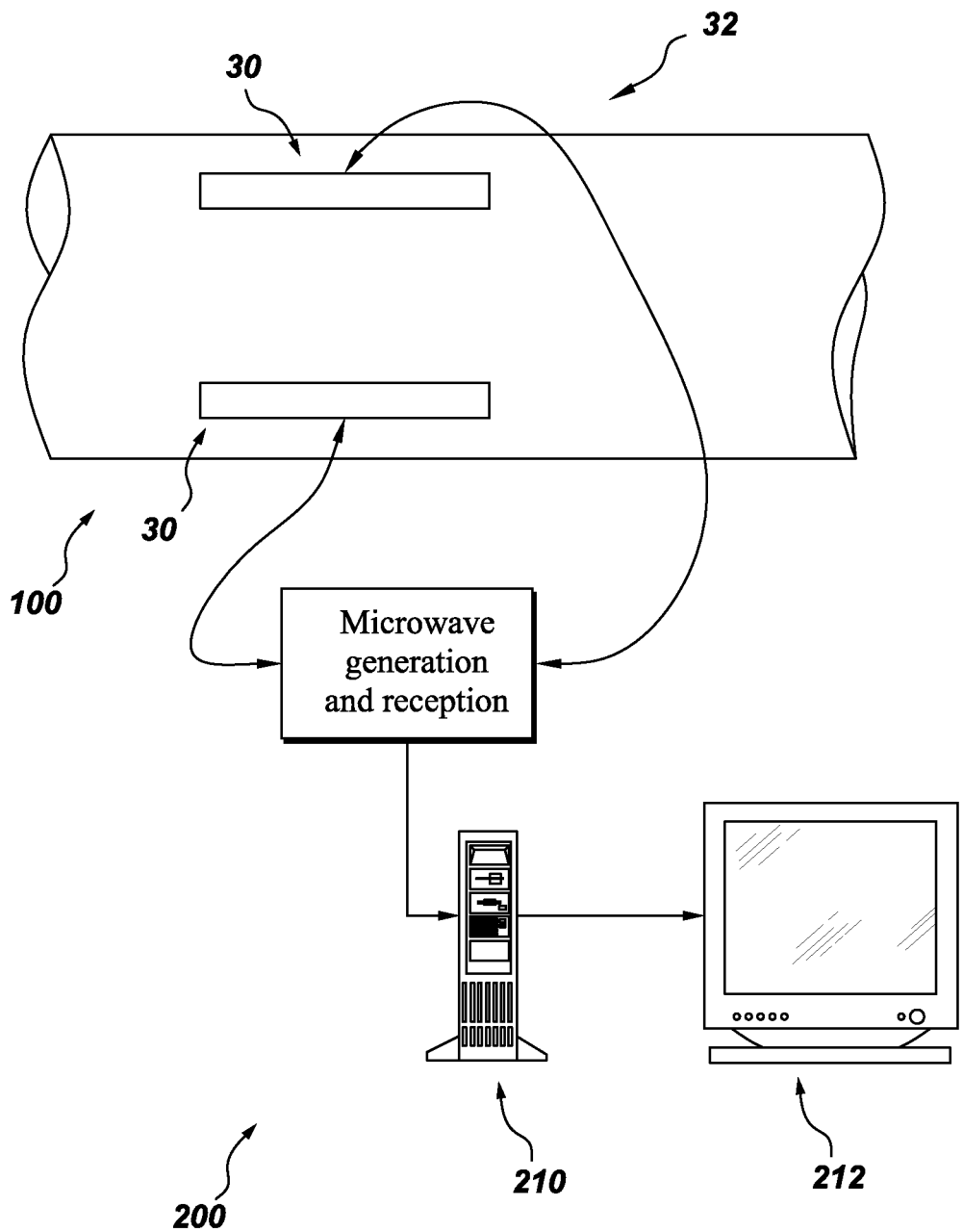
FIG. 5 is a perspective view of a multiphase flow metering system using patch antennas, according to an embodiment of the present invention.

FIG. 5 depicts a schematic figure showing a system 200 for metering multiphase flow with patch antennas in accordance with aspects of the present invention. The system 200 comprises a plurality of patch antennas 30 arranged in communication with a multiphase composition inside of a pipe 100. A single patch antenna 30 or a plurality of patch antennas 30 may be configured in any arrangement that is discussed herein. FIG. 5 merely shows two patch antennas 30 for schematic purposes only. In any event, the plurality of patch antennas 30 are connected to a source/power sensor or alternatively a network analyzer, which is then interface to a computer 210 that includes a communication device 212 (e.g., Graphical User Interface, computer screen, etc.). The communication means 32 may be cable(s), wireless connection, Internet, or any other suitable means to allow communication between the computer 210 and the configuration of patch antennas 30 at the pipe 100. The computer 210 may be any suitable computer (e.g., personal computer, cloud computing, server arrangement, computer network, etc.) in combination with software, firmware, and/or the like for providing various aspects of the method discussed herein.

Figure 6:
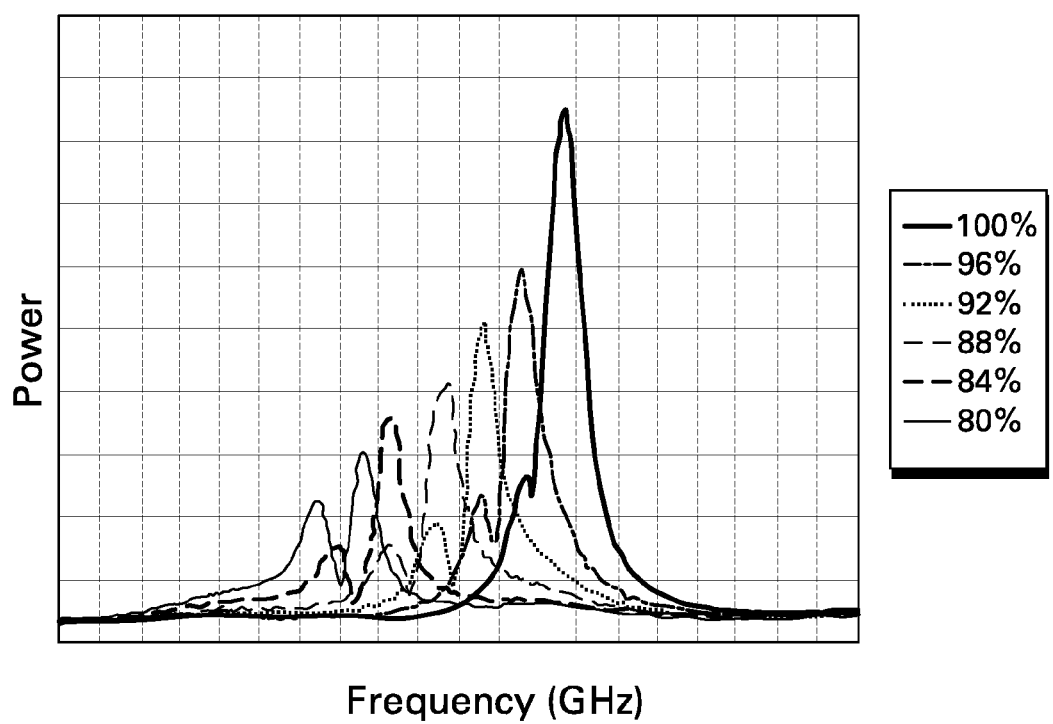
FIG. 6 is a graph showing typical frequency response plots, according to an embodiment of the present invention.
Figure 7:
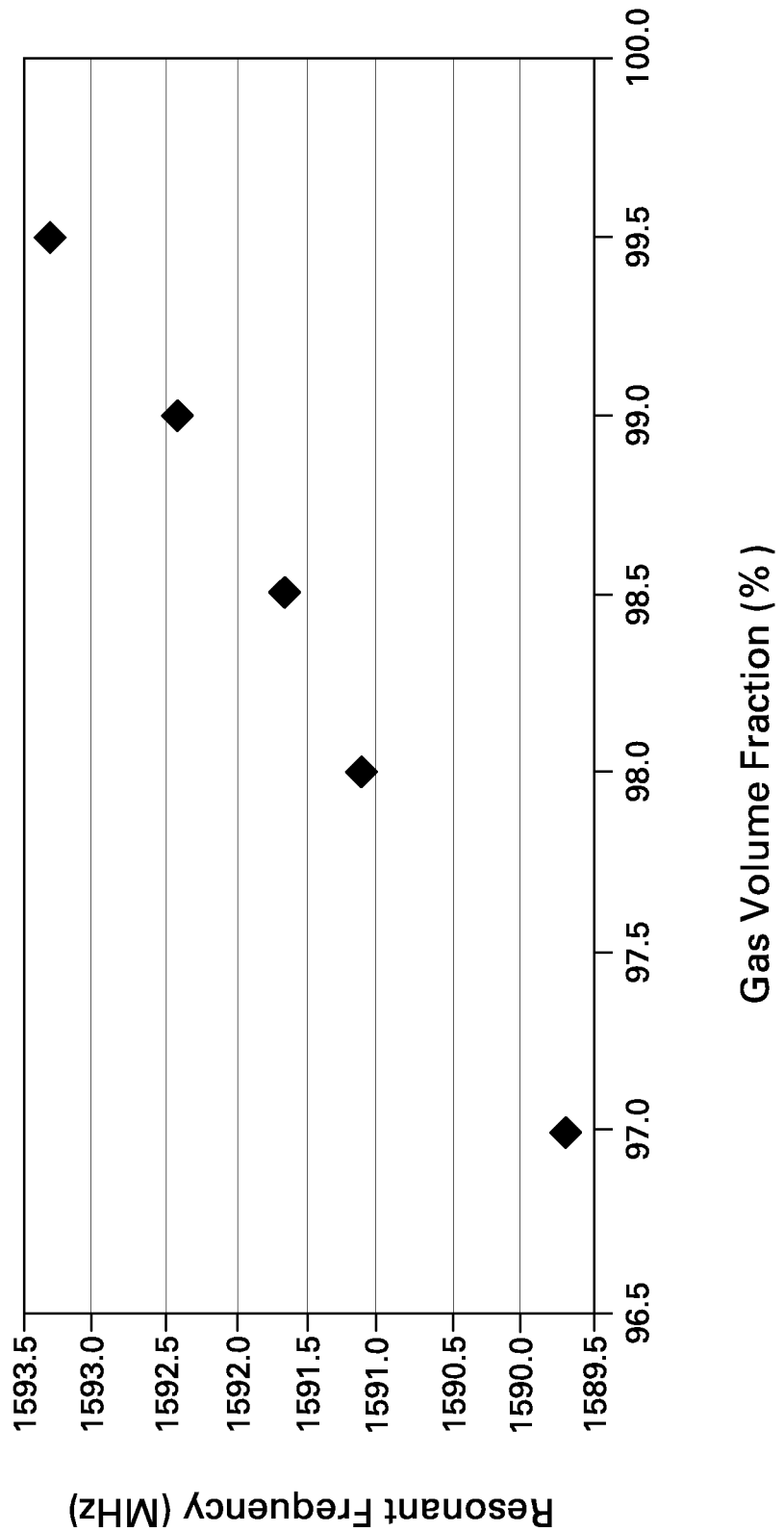
FIG. 7 is a graph showing test results, according to an embodiment of the present invention.

FIGS. 6 shows typical frequency response curves showing change in resonant frequency with composition. FIG. 7 shows the center frequency (Y-axis) as compared to the gas volume fraction (GVF) % (X-axis) for the various compositions of oil and gas. As shown, the substantially linear shift in frequency with the shift in GVF.

Figure 8:
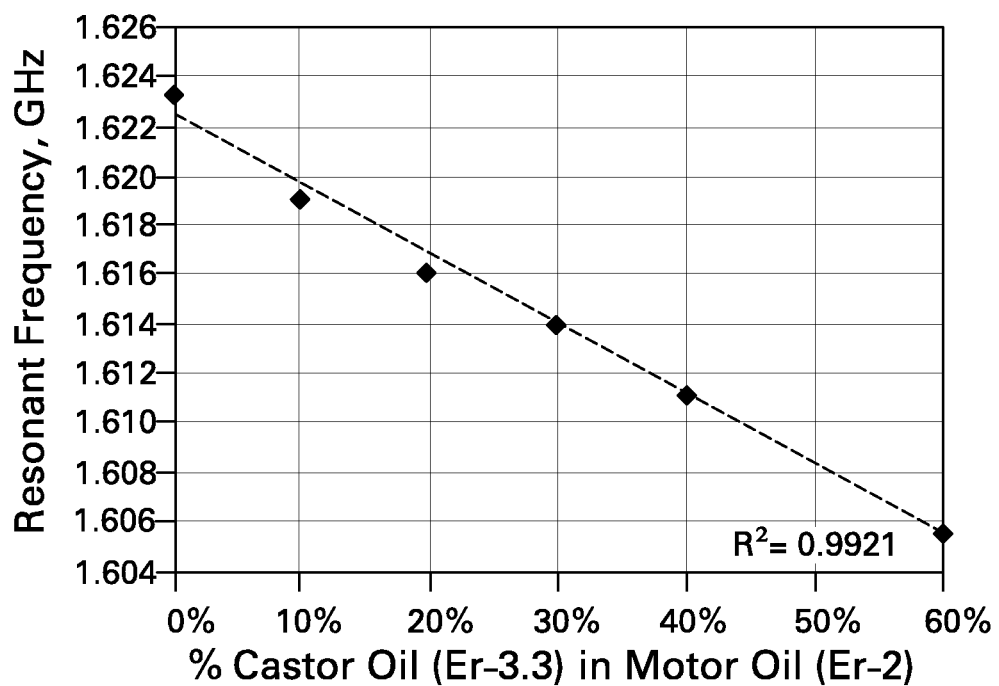
FIG. 8 is a graph showing test results, according to an embodiment of the present invention.

Similarly, FIG. 8 depicts results of additional experimental data obtained where a patch antenna configuration was used inside a 4" pipe. In this experiment, the multiphase composition comprises two oils having different permittivities (i.e., castor oil and motor oil), wherein castor oil has permittivity about 3.3 and motor oil has a permittivity about 2. The Resonant Frequency (Y-axis) is shown as compared to the percentage of Castor Oil in Motor Oil (X-Axis). As shown, the resonant frequency shifts substantially in a linear fashion with the small change in permittivity of the multiphase composition (e.g., change in percentage of castor oil).

Figure 9A:
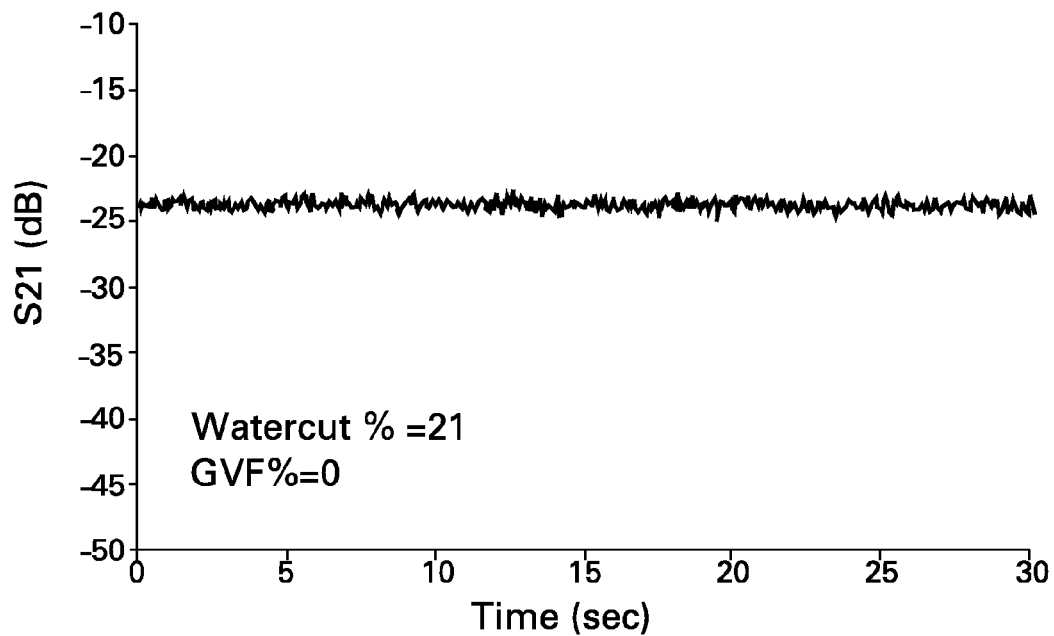
FIGS. 9A-9D are various graphs showing test results, according to various embodiments of the present invention.
Figure 9B:
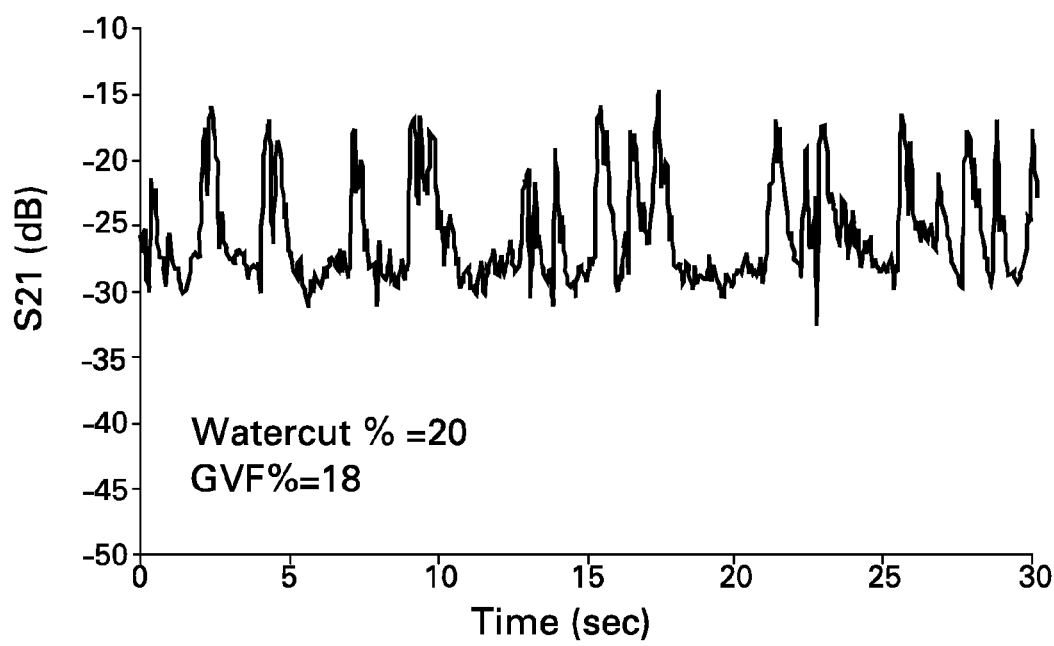
Figure 9C:
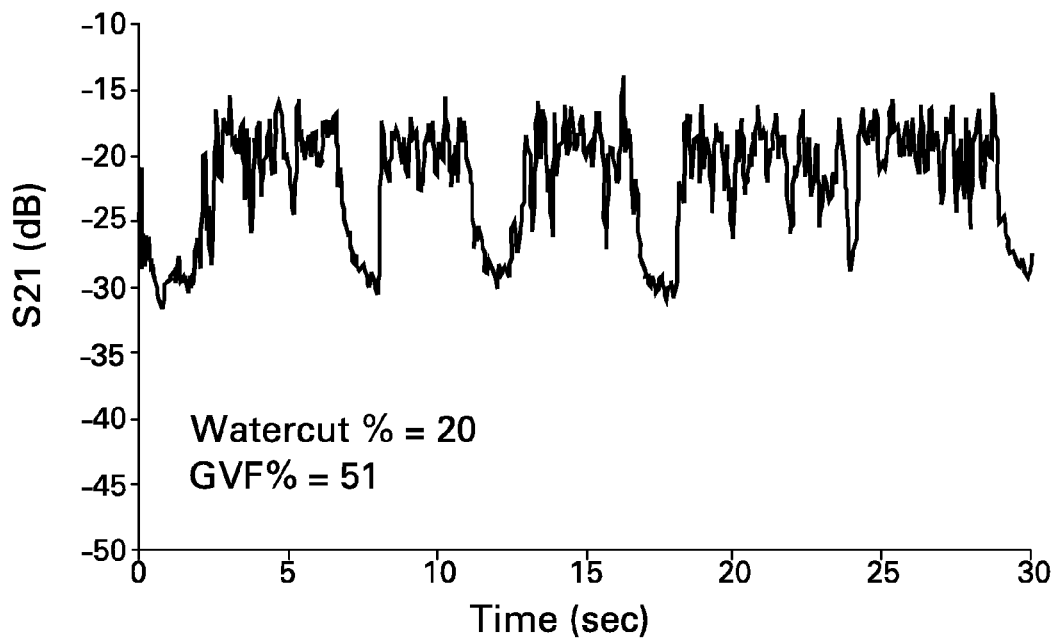
Figure 9D:
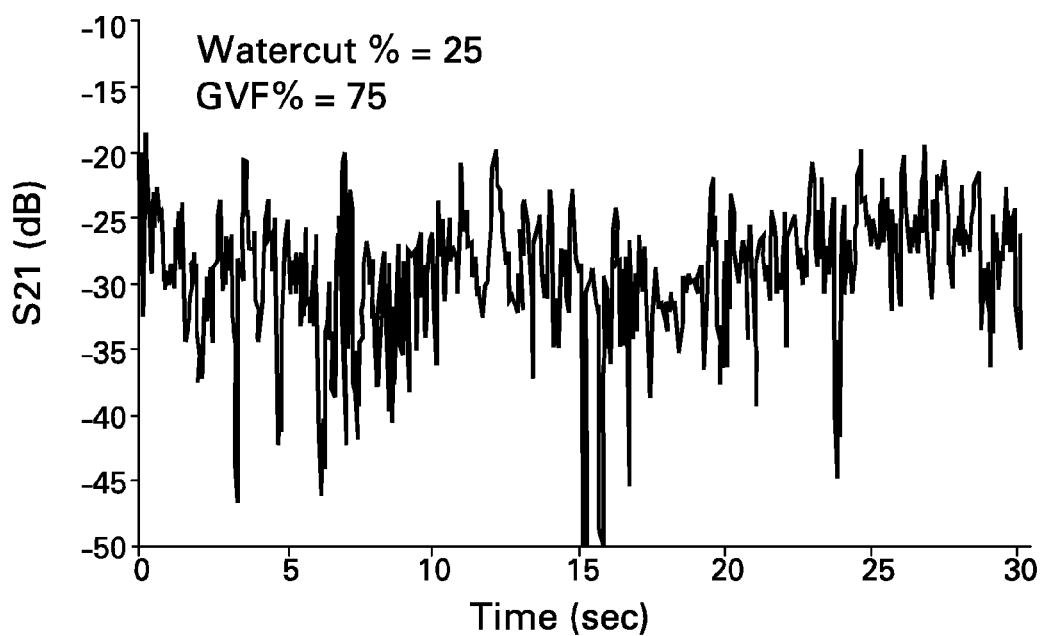

In another embodiment two or more patch antennas may be operated at a few select frequencies in a transmit-receive mode. Phase fraction estimation is done by using amplitude and phase information from transmission and using reflection coefficients. Additionally, by operating the patch antennas at the few select frequencies, the same amplitude and phase information from transmission and reflection coefficients may be used for flow regime identification. FIGS. 9A through 9D depict test results at a single frequency conducted for various multiphase compositions showing the transmitted signal strength, S21 (Y-axis) over time (X-axis). As shown, S21 connotes the measured signal at a port 2 on a pipeline due to an excitation at a port 1. Referring to FIG. 9A, the transmitted signal strength, S21, is shown for a composition having a watercut percentage of 21 and a GVF percentage of 0. Thus, the composition tested in FIG. 9A comprised about 21% water and about 79% oil. Similarly, FIG. 9B shows the test results for a multiphase composition comprising about 18% gas and about 82% liquid, of which about 20% is water and the remaining percentage is oil. Similarly, FIG. 9C shows the test results for a multiphase composition comprising about 51% gas and about 49% liquid, of which about 20% is water and the remaining percentage is oil. Finally, FIG. 9D shows the test results for a multiphase composition comprising about 75% gas and about 25% liquid, of which about 25% is water and the remaining percentage is oil. It may be seen that the signals exhibit distinct signatures depending upon the flow regime and this fact can be utilized for flow regime classification algorithms.

In another embodiment multiple measurands (e.g., phase and amplitude information of transmission and reflection coefficients, resonant frequencies and the like) can be combined into a single parameter using a transfer functions. This gives an added benefit that there is less noise or fluctuation in the results as compared to using a single parameter or measurand.

In another embodiment, two sets of patch antennas may be spaced a distance part along longitudinal axis of the pipe so that cross-correlation may be used to estimate flow velocities. In still another embodiment, the patch antennas may also act as electrodes for low frequency impedance measurements. By using the patch antenna as an electrode, EIS (Electrical Impedance Spectroscopy) methods of measurement may be employed. Additionally, in another embodiment, an array of patch antennas may be used for tomographic reconstruction. For example, the array of patch antennas may be placed circumferentially around the pipe so as to generate a tomographic image. Clearly, the patch antennas maybe used for various measurement methodologies discussed herein and otherwise.

The present invention has been described in terms of the preferred embodiment, and it is recognized that equivalents, alternatives, and modifications, aside from those expressly stated, are possible and within the scope of the appending claims.

What is claimed is:

1. A method of metering a multi-phase composition in a pipe, comprising:
locating at least one patch antenna that operates in a radio or microwave frequency range, in proximity to the multi-phase composition;
exciting the at least one patch antenna over a range of frequencies;
measuring transmitted and reflected signals over time;
estimating a baseline resonant frequency;
estimating a shift in a resonant frequency from the baseline resonant frequency;
calculating a permittivity of the multi-phase composition based on the shift in the resonant frequency; and
calculating a phase composition of the multi-phase composition based on the permittivity.

2. The method of claim 1, wherein the at least one patch antenna has a shape comprising one of a rectangle, a circle, a diamond, an ellipse, a square, or combinations thereof.

3. The method of claim 1, wherein at least a portion of the pipe is non-metallic.

4. The method of claim 1, wherein at least a portion of the pipe is metallic.

5. The method of claim 1, wherein the multi-phase composition comprises gas and a liquid.

6. The method of claim 1, wherein the locating the at least one patch antenna comprises placing a plurality of patch antennas in a helical or circular configuration so as to at least partially surround the pipe.

7. The method of claim 1, wherein the at least one patch antenna is placed on an interior surface of the pipe.

8. The method of claim 1, wherein the at least one patch antenna is placed on an exterior surface of the pipe.

9. The method of claim 1, wherein the at least one patch antenna is configured to conform to a surface of the pipe.

10. The method of claim 1, wherein the at least one patch antenna is configured to protrude into a portion of an interior flow space of the pipe.

11. The method of claim 1, further comprising placing a material transparent to microwaves between the at least one patch antenna and a surface of an interior flow space of the pipe, wherein the at least one patch antenna is recessed away from the interior flow space of the pipe.

12. The method of claim 1, wherein the at least one patch antenna further comprises a protective cover.

13. The method of claim 1, wherein the at least one patch antenna has a polarization of one of a circle, an ellipse, a rectangle, or combinations thereof.

* * * * *